US009000784B2

(12) United States Patent
Eberheim et al.

(10) Patent No.: US 9,000,784 B2
(45) Date of Patent: *Apr. 7, 2015

(54) CONDUCTIVE CONDUCTIVITY SENSOR

(75) Inventors: Andreas Eberheim, Waldheim (DE); Torsten Pechstein, Radebeul (DE); Christian Fanselow, Geringswalde (DE); Robert Scholz, Dobeln (DE)

(73) Assignee: Endress + Hauser Conducta Gesellschaft für Mess- und Regeltechnik mbH + Co. KG., Gerlingen (DE)

( * ) Notice: Subject to any disclaimer, the term of this patent is extended or adjusted under 35 U.S.C. 154(b) by 610 days.

This patent is subject to a terminal disclaimer.

(21) Appl. No.: 13/139,745

(22) PCT Filed: Nov. 20, 2009

(86) PCT No.: PCT/EP2009/065527
§ 371 (c)(1),
(2), (4) Date: Jun. 15, 2011

(87) PCT Pub. No.: WO2010/072483
PCT Pub. Date: Jul. 1, 2010

(65) Prior Publication Data
US 2011/0309848 A1 Dec. 22, 2011

(30) Foreign Application Priority Data
Dec. 15, 2008 (DE) .......................... 10 2008 054 659

(51) Int. Cl.
*G01R 27/08* (2006.01)
*G01N 27/07* (2006.01)
*B22F 3/22* (2006.01)
*C22C 29/12* (2006.01)
(Continued)

(52) U.S. Cl.
CPC ................ *G01N 27/07* (2013.01); *B22F 3/225* (2013.01); *C22C 29/12* (2013.01); *C22C 32/0031* (2013.01); *G01R 27/22* (2013.01)

(58) Field of Classification Search
USPC .......................... 324/632–643, 693–724, 71.1
See application file for complete search history.

(56) References Cited

U.S. PATENT DOCUMENTS 5,495,176 A * 2/1996 Shiranita et al. .............. 324/439
6,340,418 B1 * 1/2002 Turkdogan .................... 204/400
6,348,803 B1 * 2/2002 Mohr ............................ 324/642
(Continued)

FOREIGN PATENT DOCUMENTS

DE 7731214 4/1978
DE 3401791 8/1985
(Continued)

*Primary Examiner* — Melissa Koval
*Assistant Examiner* — Trung Nguyen
(74) *Attorney, Agent, or Firm* — Bacon & Thomas, PLLC

(57) ABSTRACT

In a conductive conductivity sensor having a probe, which is immersible in a measured medium and which comprises at least two electrodes made of a first, electrically conductive material and at least one probe body made of a second, electrically non-conductive material, the electrodes are at least partially embedded in the probe body and insulated from one another by the probe body, wherein the electrodes and the probe body are embodied as a composite workpiece. There especially exists between the first material and the second material in at least one section of a material transition between the first and the second material a secure bond, especially a bond based on intermolecular interactions or chemical bonds.

11 Claims, 4 Drawing Sheets

(51) Int. Cl.
*C22C 32/00* (2006.01)
*G01R 27/22* (2006.01)

(56) References Cited

U.S. PATENT DOCUMENTS

2009/0212807 A1* 8/2009 Chen et al. .................... 324/762
2013/0021047 A1* 1/2013 Thieme et al. ................ 324/724

FOREIGN PATENT DOCUMENTS

| | | |
|---|---|---|
| DE | 4132432 | 4/1993 |
| DE | 4214594 | 11/1993 |
| DE | 19746075 | 5/1999 |
| DE | 20016352 | 1/2001 |
| DE | 102005039290 | 2/2007 |
| DE | 102006025098 | 11/2007 |

* cited by examiner

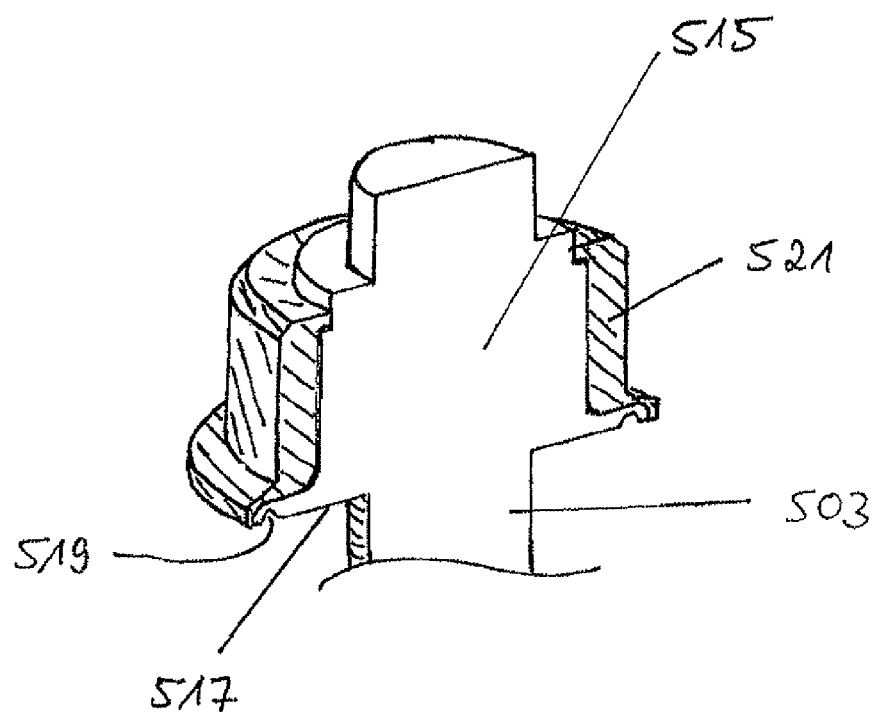

CONDUCTIVE CONDUCTIVITY SENSOR

TECHNICAL FIELD

The invention relates to a conductive conductivity sensor having a probe, which is immersible in a measured medium and which has at least two metal electrodes and at least one probe body, in which the metal electrodes are at least partially embedded.

BACKGROUND DISCUSSION

Conductive conductivity sensors known from the state of the art-e.g. from EP 990 894 B1-comprise at least two electrodes, which, for measuring, are immersed in the measured medium. For determining the electrolytic conductivity of the measured medium, the resistance or conductance of the space between the electrodes in the measured medium is determined. In the case of known cell constant, the conductivity of the measured medium can be ascertained from this determination.

In DE 10 2006 024 905 A1, an electrode arrangement of a conductive conductivity sensor is shown, in the case of which an inner and an outer electrode are isolated from one another and insulated relative to one another by a shaped seal and a seal support body. The shaped seal serves to prevent penetration of measured medium into an annular gap between the electrodes.

Such an electrode arrangement with additional seals is relatively complex from a constructive perspective. This is true especially for conductivity sensors which are intended for application in food technology or in the pharmaceutical industry. High hygienic requirements are placed on such sensors. For example, the probes of such sensors, insofar as they come in contact with the measured medium, are not allowed to have any difficulty accessible gaps. A cleaning and/or sterilizing of the entire probe surface, which contacts the measured medium, must be possible. Conventional seals or a shaped seal according to DE 10 2006 024 905 A1 can basically fulfill this purpose; however, they lead to a complex construction requiring a correspondingly complex assembly effort.

SUMMARY OF THE INVENTION

An object of the invention is consequently to provide a conductive conductivity sensor with a probe which is immersible in a measured medium, wherein the sensor overcomes the disadvantages of the state of the art, and is especially suitable for applications in the case of high hygienic requirements, and simultaneously is constructively simple and, respectively, easy to manufacture.

The object is achieved by a conductive conductivity sensor having a probe, which is immersible in a measured medium and which has at least two electrodes made of a first electrically conductive material and at least one probe body made of a second, electrically non-conductive material, wherein the electrodes are at least partially embedded in the probe body and are insulated from one another by the probe body, and wherein the electrodes and the probe body are embodied as a composite workpiece, especially a sintered composite workpiece.

By embodying the electrodes and the probe body in the form of a single composite workpiece, a gap-free material transition—and therewith also a gap-free seal—between the probe body and the electrodes at least partially embedded in the probe body is achieved. At the same time, the construction of the probe as compared to the probe known from DE 10 2006 024 905 A1 is significantly simplified, since no additional sealing measures are required. Additionally, such a composite workpiece displays an improved wear resistance compared to synthetic material seals.

In an advantageous embodiment, the electrodes and the probe body are produced by a multicomponent injection molding method with the first material as a first component and the second material as a second component. This has the advantage that a complete probe for a conductivity sensor can be produced with few working steps, without other assembly steps for applying sealing means being required. A further advantage of this embodiment is the fact that the multicomponent injection molding permits a large degree of design freedom with respect to the electrode geometry. In this way, the electrode arrangement can, for example, be optimized with regard to the cell constant of the conductivity sensor, without having to accept limitations due to requirements for the seal.

In the multicomponent injection molding, a first injection charge which comprises the first material and a second injection charge which comprises the second material are injected into an injection mold either simultaneously or one after the other. The green body thus produced is debindered and sintered, and a composite workpiece is thus formed.

The composite workpiece thus manufactured has a secure bond between the first material and the second material in at least one section of a material transition between the first and the second material. This secure bond is at least partially based on intermolecular interactions or chemical bonds between regions of the first material and regions of the second material. In this way, there results an intimate connection between the electrodes and the probe body, this connection acting as a gap-free seal.

In an embodiment, the first material is a conductive ceramic or a metal, especially platinum, titanium or stainless steel.

In an advantageous embodiment, the second material is a synthetic material or a ceramic, especially aluminum oxide ceramic ($Al_2O_3$), chromium oxide ceramic ($Cr_2O_3$), titanium dioxide ceramic ($TiO_2$), tialite ceramic ($Al_2TiO_5$) or zirconium dioxide ceramic ($ZrO_2$).

In an especially advantageous further development, the electrodes are made of platinum and the probe body of $Al_2O_3$ ceramic. Since platinum and $Al_2O_3$ ceramic possess very similar thermal coefficients of expansion, the secure bond between the electrodes and the probe body is preserved even over a large temperature range, for instance, a range of −30° C. to 300° C.

In an alternative, likewise very advantageous, further development, the electrodes are made of titanium or stainless steel and the probe body of $ZrO_2$ ceramic. Also in the case of this combination, the thermal coefficients of expansion of the electrode material and probe body material are similar, so a stable connection between the electrodes and probe body is assured over a large temperature range, especially also in the case of temperature changes during use of the conductivity sensor for monitoring a process.

In an embodiment, the electrodes are embedded in the probe body in such a manner, that only their end faces are exposed within an end face of the probe body. In this way, the surface of the probe which is immersible in the medium is free of projections on which particles could remain clinging, so that a fouling of the probe is largely prevented.

In an additional embodiment, the electrodes are embodied as tubes with different inner diameters, wherein the tubes are arranged coaxially about a shared symmetry axis in such a manner, that the tube with the larger inner diameter surrounds the tube with the smaller inner diameter. Preferably, the inner tube is internally filled, i.e. is embodied as a rod.

This construction is especially advantageous when the conductivity sensor is embodied as a conductive conductivity sensor with four electrodes. In this case, in an advantageous embodiment, the end faces of two electrodes can in each case be exposed in two surfaces of the probe body which lie opposite one another, especially oppositely lying surfaces of a rectangular groove of the probe body. In the case of the electrode pairs, one electrode is in each case connectable as an electrical current electrode, and one as a voltage electrode. In this way, a closed field forms between the electrodes, this being especially advantageous for minimizing the influence of walls in the surrounding environment.

In an advantageous embodiment, the conductive conductivity sensor furthermore includes a process connection. Ideally, the process connection is a component of the platform of the probe, i.e. embodied as one-piece with the probe body, i.e. embodied as a single formed part. For this, a suitably formed die is provided during the injection molding. This has the advantage that the process connection is also gap free, so that gap freedom of the entire conductivity sensor is assured. In a further development, for improving mechanical stability or for securement of the sensor, metal parts or parts made of synthetic material can be provided on the side of the process connection facing away from the process.

A method for manufacturing a conductive conductivity sensor in one of the previously described embodiments includes steps of: injecting the first and the second material in a multicomponent injection molding method, especially a multicomponent powder injection molding method, simultaneously, or in a two stage injection molding method one after the other, into a mold cavity for producing a green body, debindering and sintering the green body for producing a composite workpiece, which includes electrodes made of the first material and a probe body made of the second material.

With this method, an option is to produce the desired secure bond between the electrodes made of the first material and the probe body made of the second material at least in a section of a material transition between the first and the second material, especially based on intermolecular interactions or chemical bonds.

In a special embodiment of this method, the first material, in a first stage, is injection molded in its own mold, so that a green body forms, wherein, in a second stage, the green body, is transferred into an additional mold and injection molded around with the second material.

The invention will now be explained in greater detail on the basis of the appended drawing, the figures of which show as follows:

BRIEF DESCRIPTION OF THE DRAWINGS

FIG. 5 is a process connection for a probe according to one of the embodiments of FIGS. 1 to 4.

DETAILED DISCUSSION IN CONJUNCTION WITH THE DRAWINGS

Figure 1:
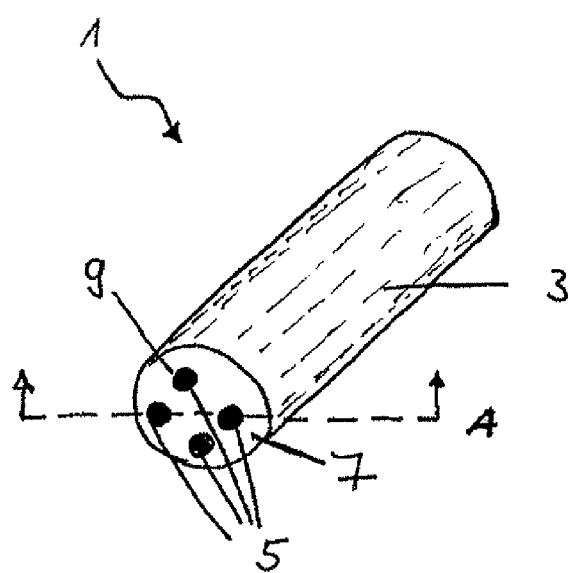
FIG. 1 is a probe of a conductivity sensor according to an embodiment of the invention.
Figure 2:
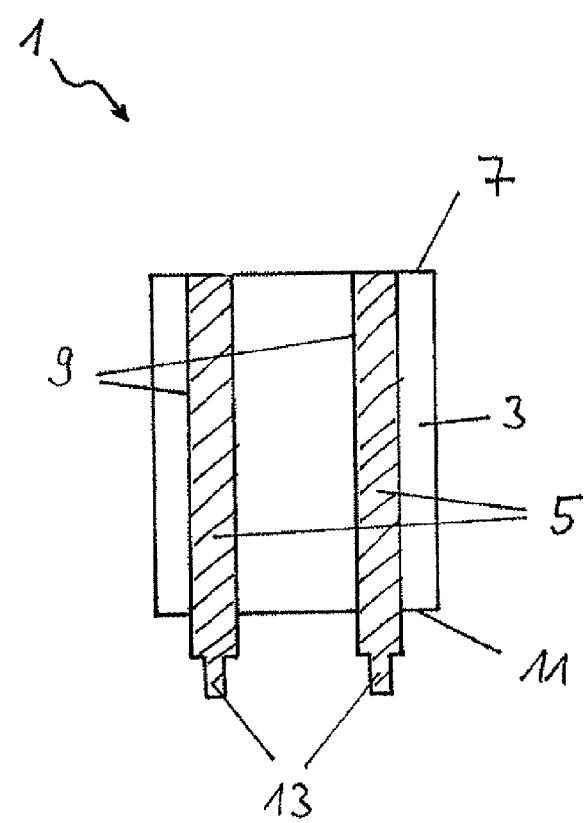
FIG. 2 is a longitudinal sectional representation through the probe shown in FIG. 1.

FIGS. 1 and 2 show the probe 1 of a conductivity sensor, wherein the probe is immersible in a measured medium, and has a probe body 3 made of an electrically non-conductive material, and electrodes 5, made of an electrically conductive material and embedded in the probe body. Electrodes 5 and probe body 3 are together embodied as a composite workpiece. On the end face 7 of probe body 3, the end faces of electrodes are exposed, and, in a conductivity measuring, are in contact with the measured medium. FIG. 1 shows a perspective representation of probe 1 with a view of that end face 7 of the probe which, in the case of a conductivity measuring, is immersed into the measured medium. FIG. 2 shows a longitudinal section through the probe taken according to the cutting plane A in FIG. 1.

The probe 1 shown in FIGS. 1 and 2 forms the measuring probe of a so-called 4-electrode sensor, this probe being immersible in a measured medium. Two of electrodes 5, especially two electrodes 5 adjoining directly on one another, are operated as so-called electrical current electrodes. The two remaining electrodes 5 are operated as so-called voltage electrodes. In measurement operation, an alternating voltage is applied between the two electrical current electrodes, and an alternating electrical current is fed therewith into the measured medium. The potential difference occurring between the voltage electrodes is measured, especially via a currentless measuring. From the fed-in alternating electrical current and the measured potential difference, the impedance of the conductivity measurement cell formed by immersion of probe 1 in a measured medium is calculated, from which, taking into consideration the cell constant, the specific resistance or conductivity of the measured medium can be ascertained. A measurement transmitter (not shown) connected to the probe 1 for regulating or controlling the fed-in, alternating current serves also for measuring the potential difference of the voltage electrodes and for converting the measured values into a resistance or conductance value or a specific resistance or specific conductivity of the measured medium. The measuring electronics can be a component of the measurement transmitter or can, at least partially, be accommodated in a separate module, for example, in a plug head connected with probe 1. The ascertained measured value can be displayed either by the measurement transmitter or output to a superordinated control system.

Probe body 3 and electrodes 5 are, in each case, stylus-shaped, i.e. embodied as elongated cylinders with round cross sectional areas. The electrodes 5 extend beyond the cylindrical base 11 of probe body 3 facing away from the measured medium, and are provided with connections 13, via which electrodes 5 can be connected with a regulator or controller (open, or closed, loop control) of the fed-in, alternating current and, respectively, with a measuring electronics for determining the potential difference between the two voltage electrodes.

Figure 3:
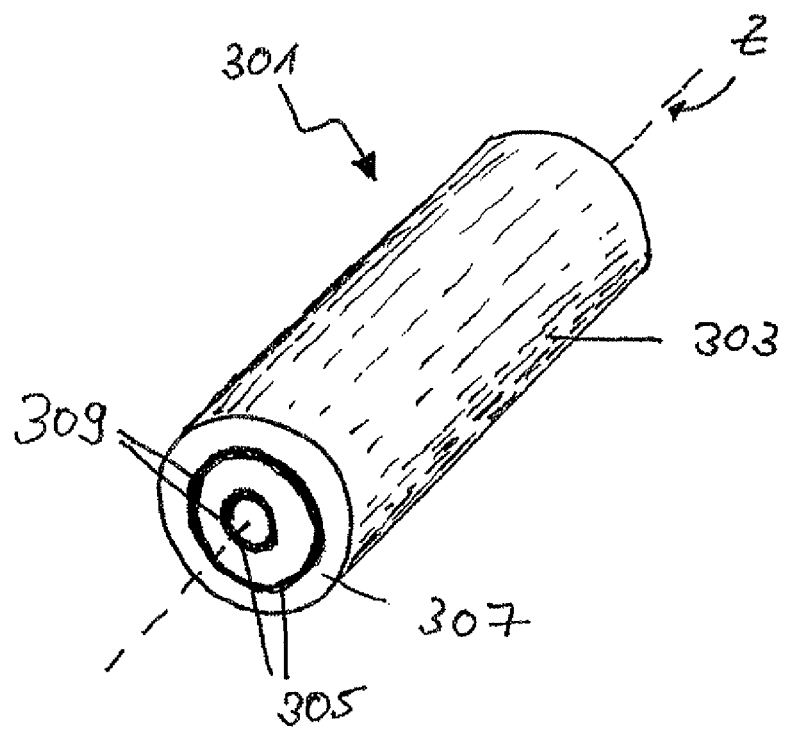
FIG. 3 is a probe of a conductivity sensor according to another embodiment of the invention.

FIG. 3 shows an alternative embodiment in the form of a probe 301 for conductive conductivity measuring, in the case of which the electrodes 305 are embodied as tubes arranged coaxially around a shared, rotational symmetry axis Z and are embedded in the sensor body 303 and insulated from one another. Exposed on the end face 307 of the sensor body 303 are the annular end faces of the electrodes. Probe 301 is embodied as a measuring probe of a 2-electrode sensor. In the case of this type of sensor, in measurement operation, an alternating voltage is applied to the two electrodes 305. Making use of a measurement transmitter (not shown) connected with electrodes 305, the impedance of the conductivity measurement cell formed by the measuring probe immersed in the measured medium is ascertained. From this, taking into consideration the cell constant, the specific resistance or the specific conductivity of the measured medium can be ascertained. The ascertained measured values can either be displayed by the measurement transmitter or output to a superordinated control system. A portion of the functions of the measurement transmitter can be executed by a measuring electronics accommodated in a separate housing outside of the measurement transmitter housing. This measuring electronics can, at least in part, be accommodated, for example, in a plug head connected with probe 301.

Figure 4:
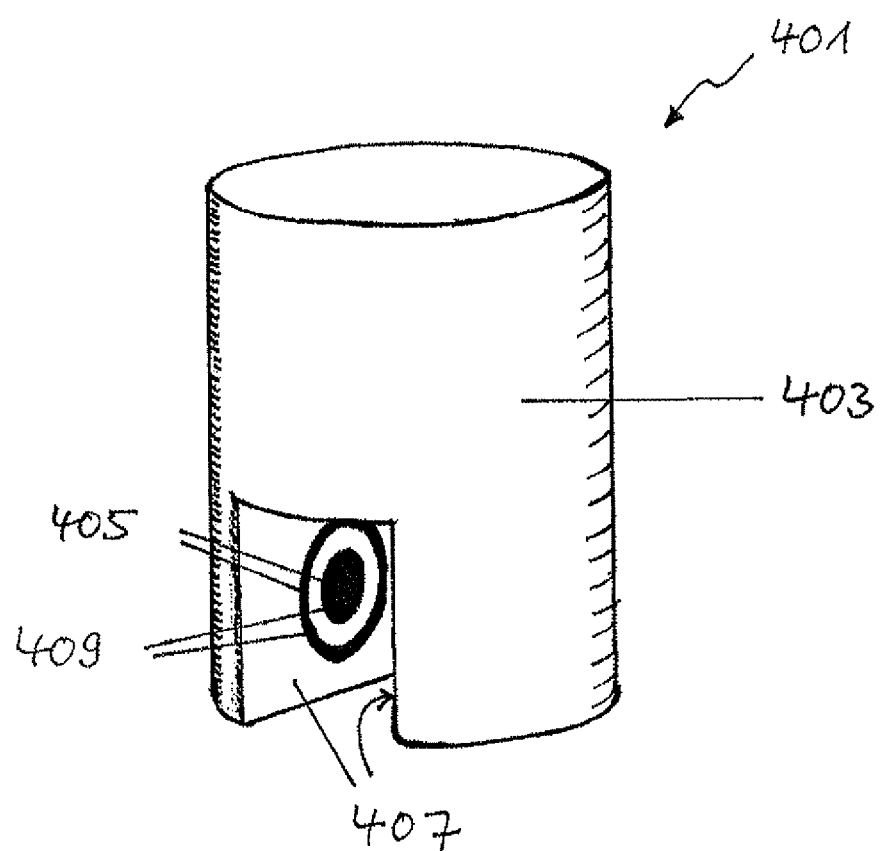
FIG. 4 is a probe of a conductivity sensor according to a further embodiment of the invention.

FIG. 4 shows an alternative embodiment of a probe 401 with a probe body 403 and four electrodes 405. In the end region of probe 401 lying opposite the process connection of the cylindrical probe body 403, a groove with rectangular cross section is provided. In two groove surfaces 407 lying opposite one another, two end faces of electrodes 405, which otherwise are embedded in probe body 403, lie, in each case exposed. One of the two electrode end surfaces exposed in an area 407 is embodied as a circular area, while the other electrode end surface surrounds the first electrode end surface as a concentric annular area. On the oppositely lying area 407, the two electrode end surfaces are arranged in an identical manner; this is, however, hidden in FIG. 4. In each case, one of the two electrodes 405 lying exposed in the oppositely lying surfaces 407 is embodied as a voltage electrode, while the other electrode of the same area is correspondingly embodied as an electrical current electrode. The electrical field forming between electrodes 405 in measurement operation is located as a closed field within the groove of the probe body 403. In comparison to the embodiments of the probe according to FIG. 1 or 3, in the case of which a free field forms, this embodiment has the advantage that the measuring cannot be affected by the influence of, for example, a wall present in the vicinity of the probe.

Electrodes 405 can, similarly to the example in FIG. 2, be contacted via connections led out from the probe body 403 (not shown in FIG. 4).

@The probes 1, 301 and 401 illustrated in FIGS. 1 to 4 are produced according to a two component, injection molding method. In the case of this method, preferably an injection molding machine with two injection units is used. In the case of application of one injection unit for the electrode material and the other injection unit for the material of the sensor body, the two injection units are preferably controlled independently of one another, since, in this way, a larger variety of electrode geometries can be produced. Two component, injection molding is an established technology especially for the manufacture of components from different synthetic materials.

Injection molding of metals or ceramics—for example, by means of metal powder, injection molding (MIM—Metal Injection Moulding) or ceramic powder, injection molding (CIM—Ceramic Injection Moulding)—is a known and established manufacturing method for technically demanding and complex, molded parts. Multicomponent injection molding of metals and/or ceramics as individual components is also known, in principle; however, it has not hitherto been usual for manufacturing composite workpieces from metal and ceramics.

Suitable as material for probe body 3, 303 or 403, is, for example, a ceramic, such as e.g. $Al_2O_3$ ceramic or a $ZrO_2$ ceramic. For electrodes 5, a material such as a metal or a conductive ceramic can be used. As a starting material for the injection molding, commercial-grade, sinterable powder with a suitable grain size can be used. Preferably, for electrodes 5, 305, 405 and probe body 3, 303, 403, such materials are used, whose thermal coefficients of expansion differ from one another only to a small degree, i.e. those whose thermal coefficients of expansion deviate from one another preferably only by $1 \cdot 10^{-6}$ to $2 \cdot 10^{-6}$/K. Thus, for example, in the case of platinum as an electrode material, which has a thermal coefficient of expansion of $8.9 \cdot 10^{-6}$/K, this can be paired with an $Al_2O_3$ ceramic with an expansion coefficient of 6 to $8 \cdot 10^{-6}$/K. In the case of titanium as an electrode material, which has a coefficient of expansion of $10.8 \cdot 10^{-6}$/K, a $ZrO_2$ ceramic with a coefficient of expansion of 10 to $12 \cdot 10^{-6}$/K can be used, for example, as a material for the probe body. A $ZrO_2$ ceramic is likewise suitable for combination with stainless steel as an electrode material, since stainless steel possesses a thermal coefficient of expansion of about $13 \cdot 10^{-6}$/K.

For injection molding, the starting materials are mixed with a binder. The injection molding charges with binder are injected into a mold cavity and a green body is thus formed. In the case of manufacture of a probe 1, 301, 401 of the invention, electrodes 5, 305, 405 and probe body 3, 303, 403 can be produced simultaneously with the assistance of a suitable injection molding die. Alternatively, a transfer technology of the multicomponent injection molding can be applied, in the case of which the electrodes 5, 305, 405 are first injection molded in their own die. The green body thus produced is transferred to a further injection molding die and injection molded around with the injection molding charge for probe body 3, 303, 403. In the case of both method variants, after the injection molding, the electrodes and the probe body are together debindered and sintered via thermal treatment.

During the sinter process, a secure bond forms between electrodes 5, 305, 405 and probe body 3, 303, 403. A composite workpiece is thus formed, which comprises both electrodes 5, 305, 405 as well as also probe body 3, 303, 403. In such case, the circumferential electrode surface 9, 309, 409 embedded in the probe body 3, 303, 403 has, at least in one or more portions of the surface 9, 309, 409, a gap-free transition to the surrounding material of probe body 3, 303, 403.

In order to assure a sufficiently secure bond, it is sufficient when, in some portions of the material transition, attractive intramolecular interactions or chemical bonds between the electrode material and the material of the probe body dominate. Among these portions are especially to be understood regions of individual microcrystallites of the sintered polycrystalline materials which in each case lie on the surface; however, individual portions can also comprise a larger region of mutually contacting surfaces of the electrodes and the probe body.

It is especially advantageous, especially with regard to the previously described hygienic requirements in the fields of the pharmaceutical industry or food technology, when the process connection of the conductivity sensor is embodied as a component of the probe body of the measuring probe. An example of such an embodiment of the probe is shown in FIG. 5. The cylindrical probe body 503 transitions at its connection end into a process connection 515 made of ceramic, which has a flange-like connecting end surface 517 adjoining directly on probe body 503. This can be connected with a process-side flange connection in a manner sealed to liquid. The connecting end surface 517 includes an annular groove 519 for accommodating a sealing ring. Process connection 515 and probe body 503 are formed as one-piece from the same material, preferably a ceramic, for example, one of the initially named ceramics. Preferably, in the case of the above-described injection molding method, the process connection and probe body are, making use of a suitably formed die, produced directly as a single formed part. In probe body 503 and in process connection 515, the electrodes of the probe are embedded as shown in FIGS. 1 to 4 (not shown in FIG. 5). In a region of process connection 515 facing away from the process, connections are provided via which the electrodes can be connected with a control or regulating electronics or with a measuring electronics.

For improving mechanical stability, or for securement of further sensor parts, such as, for example, a sensor plug head, with a housing which surrounds at least a part of the measuring electronics, or a connection to a measurement transmitter, a jacketing ring 521 made of metal or synthetic material is arranged on the side of the process connection 515 facing away from the process.

The invention is not limited to the illustrated examples of embodiments and includes all other technically possible types of implementation which fall within the scope of the following claims. Thus, each of the probes shown in FIGS. 1 to 4, for example, can be equipped with a process connection according to FIG. 5.

The invention claimed is:

1. A conductive conductivity sensor having:
    a probe, which is immersible in a measured medium and which comprises at least two electrodes made of a first, electrically conductive material and at least one probe body made of a second, electrically non-conductive material, wherein:
    said at least two electrodes are at least partially embedded in said at least one probe body and are insulated from one another by said at least one probe body;
    said at least two electrodes and said at least one probe body are embodied as a composite workpiece; and
    said at least two electrodes are embedded in said at least one probe body in such a manner, that their end faces are exposed within an end face of said at least one probe body.

2. The conductive conductivity sensor as claimed in claim 1, wherein:
    said composite workpiece is produced by a multicomponent injection molding method with said first material as first component and said second material as second component.

3. The conductive conductivity sensor as claimed in claim 1, wherein:
    said first material comprises a conductive ceramic or a metal, especially platinum, titanium or stainless steel.

4. The conductive conductivity sensor as claimed in claim 1, wherein:
    said second material comprises a synthetic material or a ceramic, especially aluminum oxide ($Al_2O_3$) ceramic, chromium oxide ($Cr_2O_3$) ceramic, titanium dioxide ($TiO_2$) ceramic, tialite ($Al_2TiO_5$) ceramic or zirconium oxide ($ZrO_2$) ceramic.

5. The conductive conductivity sensor as claimed in claim 1, wherein:
    said at least two electrodes are made of platinum and said at least one probe body is made of $Al_2O_3$ ceramic.

6. The conductive conductivity sensor as claimed in claim 1, wherein:
    said at least two electrodes are made of titanium or stainless steel and said at least one probe body is made of $ZrO_2$ ceramic.

7. The conductive conductivity sensor as claimed in claim 1, wherein:
    said at least two electrodes are embodied as tubes, and said tubes are arranged coaxially around a shared axis.

8. The conductive conductivity sensor as claimed in claim 1, further having:
    a process connection.

9. The conductive conductivity sensor as claimed in claim 8, wherein:
    said process connection is embodied as one-piece with said at least one probe body.

10. A method for the manufacture of a conductive conductivity sensor, having: a probe, which is immersible in a measured medium and which comprises at least two electrodes made of a first, electrically conductive material and at least one probe body made of a second, electrically non-conductive material, said at least two electrodes are at least partially embedded in said at least one probe body and are insulated from one another by said at least one probe body; and said at least two electrodes and said at least one probe body are embodied as a composite workpiece; the method comprising the steps of:
    injecting the first and second materials in a multicomponent injection molding method, especially a multicomponent powder injection molding method, simultaneously, or in a two stage multicomponent injection molding method one after the other, into a mold cavity for producing a green body; and
    debindering and sintering the green body for producing a composite workpiece, which includes electrodes made of the first material and a probe body made of the second material, wherein:
    in said first step, the first material is injected in a first stage into its own mold, so that a green body forms; and
    said green body is transferred in a second stage into another mold and injected around with the second material.

11. A conductive conductivity sensor, having:
    a probe, which is immersible in a measured medium and which comprises at least two electrodes made of a first, electrically conductive material and at least one probe body made of a second, electrically non-conductive material, wherein:
    said at least two electrodes are at least partially embedded in said at least one probe body and are insulated from one another by said at least one probe body;
    said at least two electrodes and said at least one probe body are embodied as a composite workpiece;
    the conductivity sensor has at least four electrodes; and
    in each case, the end faces of two electrodes are exposed in a respective one of two surfaces of said at least one probe body, which lie opposite one another.

* * * * *